United States Patent
Chapman et al.

(10) Patent No.: US 10,463,279 B2
(45) Date of Patent: Nov. 5, 2019

(54) MOVEMENT MONITORING SYSTEMS AND METHODS

(71) Applicant: Trustees of Dartmouth College, Hanover, NH (US)

(72) Inventors: Ryan Chapman, West Lebanon, NH (US); Douglas Wayne Van Citters, Hanover, NH (US); Wayne Edward Moschetti, Hanover, NH (US); John-Erik Bell, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 252 days.

(21) Appl. No.: 15/436,577

(22) Filed: Feb. 17, 2017

(65) Prior Publication Data
US 2017/0238849 A1   Aug. 24, 2017

Related U.S. Application Data

(60) Provisional application No. 62/297,425, filed on Feb. 19, 2016.

(51) Int. Cl.
*A61B 5/11*   (2006.01)
*A61B 5/00*   (2006.01)

(52) U.S. Cl.
CPC .......... *A61B 5/1121* (2013.01); *A61B 5/0024* (2013.01); *A61B 5/4576* (2013.01); *A61B 5/4585* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 2010/0090834 A1* | 4/2010 | Buchnick | A61B 5/1117 340/573.1 |
| 2013/0217998 A1* | 8/2013 | Mahfouz | G16H 50/50 600/409 |
| 2016/0302721 A1 | 10/2016 | Wiedenhoefer et al. | |

FOREIGN PATENT DOCUMENTS

WO   WO-2015164706 A1 * 10/2015  .......... A61B 5/6828

OTHER PUBLICATIONS

Bourne et al., Patient satisfaction after total knee arthroplasty: who is satisfied and who is not? Clinical Orthopaedics and Related Research. Jan. 2010;468(1):57-63.
Burns et al., Cost effectiveness of revision total knee arthroplasty. Clinical Orthopaedics and Related Research. May 2006;446:29-33.
(Continued)

*Primary Examiner* — Paul M. West
*Assistant Examiner* — Mark A Shabman
(74) *Attorney, Agent, or Firm* — Wolf, Greenfield & Sacks, P.C.

(57) ABSTRACT

Systems and methods for monitoring a range of motion of a joint are described. For example, in one embodiment, a first set of sensors may sense accelerations of a first body portion located on a first side of the joint and a second set of sensors may sense accelerations of the second body portion located on a second opposing side of the joint. The acceleration data may then be used to compute the relative motion of the first and second body portions to determine movement of the joint. This joint movement may then be used to determine one or more range of motion movement metrics which are output for viewing by a subject or medical practitioner.

30 Claims, 9 Drawing Sheets

(56) References Cited

OTHER PUBLICATIONS

Elias et al., Footedness is a better predictor than is handedness of emotional lateralization. Neuropsychologia. 1998;36(1):37-43.

Endo et al., A model of muscle-tendon function in human walking at self selected speed. IEEE Transactions on Neural Systems and Rehabilitation Engineering. Mar. 2014;22(2):352-62.

Ghazinouri et al., Total Knee Arthroplasty Protocol. Brigham and Women's Hospital, Inc., Department of Rehabilitation Services. 2007:1-7.

Kang et al., Effects of walking speed, strength and range of motion on gait stability in healthy older adults. Journal of Biomechanics. 2008;41:2899-905.

Kerrigan et al., Biomechanical gait alterations independent of speed in the healthy elderly: Evidence for specific limiting impairments. Arch Phys Med Rehabil. Mar. 1998;79:317-22.

Kremers et al., Prevalence of Total Hip and Knee Replacement in the United States. Journal of Bone and Joint Surgery. Sep. 2, 2015;97A(17):1386-97.

Kurtz et al., Projections of primary and revision hip and knee arthroplasty in the United States from 2005 to 2030. Journal of Bone and Joint Surgery. Apr. 2007;89A(4):780-5.

Lavernia et al., The increasing financial burden of knee revision surgery in the United States. Clinical Orphaedics and Related Research. May 2006;446:221-226.

Losina et al., Cost-effectiveness of total knee arthroplasty in the United States: patient risk and hospital volume. Arch Intern Med. Jun. 22, 2009:169(12):1113-22.

Mann et al., Biomechanics of walking, running, and sprinting. The American Journal of Sports Medicine. 1980;8(5):345-50.

McClelland et al., Gait analysis of patients following total knee replacement: a systematic review. The Knee. 2007;14:253-63.

McMahon et al., The risk of contralateral total knee arthroplasty after knee replacement for osteoarthritis. Journal of Rheumatology. 2003;30(8):1822-4.

Milner, Is gait normal after total knee arthroplasty? Systematic review of the literature. Journal of Orthopaedic Science. 2009;14:114-20.

Noble et al., Patient Expectations Affect Satisfaction with Total Knee Arthroplasty. Clinical Orthopaedics and Related Research. Nov. 2006;452:35-43.

Ong et al., Prevalence and Costs of Rehabilitation and Physical Therapy After Primary TJA. The Journal of Arthroplasty. 2015;30:1121-6.

Robertsson et al., Patient satisfaction after knee arthroplasty: a report on 27,372 knees operated on between 1981 and 1995 in Sweden. Acta Orthopaedica Scandinavica. 2000;71(3):262-7.

Smith et al., Pre-surgery knee joint loading patterns during walking predict the presence and severity of anterior knee pain after total knee arthroplasty. Journal of Orthopaedic Research. 2004;22:260-6.

Van Citters et al., Developing a pathway for high-value, patient-centered total joint arthroplasty. Clinical Orthopaedics and Related Research 2014;472(5):1619-35.

* cited by examiner

MOVEMENT MONITORING SYSTEMS AND METHODS

CROSS REFERENCE TO RELATED APPLICATIONS

This application claims the benefit of priority under 35 U.S.C. § 119(e) of U.S. provisional application Ser. No. 62/297,425, filed Feb. 19, 2016, the disclosure of which is incorporated herein by reference in its entirety.

GOVERNMENT FUNDING

This invention was made with government support under grant # UL1 TR001086 awarded by the National Institutes of Health. The government has certain rights in the invention.

FIELD

Disclosed embodiments are related to movement monitoring systems and methods.

BACKGROUND

With greater than one million joint replacement procedures performed annually, joint arthroplasty is one of the most common elective surgical procedures performed in the United States. Despite its high success rate with respect to subject satisfaction and pain reduction, joint arthroplasty accounts for nearly $31 billion in hospital charges for the procedure alone. Moreover, post-operative physical therapy (PT) accounts for an additional 10% or roughly $3.1 billion annually. Assessing the recovery of a replaced joint postoperatively requires subjects to return to the hospital semi-regularly over 12 postoperative months for singular joint range of motion (ROM) measurements. This is inconvenient, costly, and has limited scope clinically.

In addition to the above, the high cost of post-operative physical therapy (PT) is in part due to a 'one-size-fits-all' implementation for recovery. Specifically, subjects are sent through the same quantity and rigor of physical therapy regardless of other factors following a joint replacement procedure. This type of implementation results in successful postoperative rehabilitation for the vast majority of subjects. Unfortunately, it forces some subjects to participate in PT who would otherwise recover well without any post-operative intervention. This is a gross misuse of a time and money (i.e. personal patient dollars and healthcare system dollars) for patients, physical therapists, and physicians. A second source of the high costs associated with postoperative PT is misdiagnosing a subject who needs more aggressive PT. For example, there are some subjects who do not recover as desired, and if these subjects are not identified early enough, the eventual PT intervention may require musculoskeletal manipulations under anesthesia instead of less expensive and less invasive interventions.

SUMMARY

In one embodiment, a movement monitoring system includes a first set of sensors attachable to a first body portion associated with a first side of a joint and a second set of sensors attachable to a second body portion associated with a second side of the joint. The first set of sensors sense at least one of linear acceleration, rotational velocity, and orientation of the first body portion. Additionally, the second set of sensors sense at least one of linear acceleration, rotational velocity, and orientation of the second body portion.

In another embodiment, a method for monitoring a range of motion of a joint includes: computing the relative motion of a first body portion associated with a first side of a joint and a second body portion associated with a second side of the joint using a first data set associated with the first body portion and a second data set associated with the second body portion; computing movement of the joint based on the relative motion of the first body portion and the second body portion; calculating one or more range of motion movement metrics for the joint; and outputting the one or more range of motion movement metrics in a viewable format.

In yet another embodiment, a method includes: determining a movement metric for a joint of a subject; determining a difference between the determined movement metric and a standard movement metric; determining if intervention is needed for the subject based at least in part on the difference between the determined movement metric and the standard movement metric; and outputting an indication of whether or not intervention for the subject is needed.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
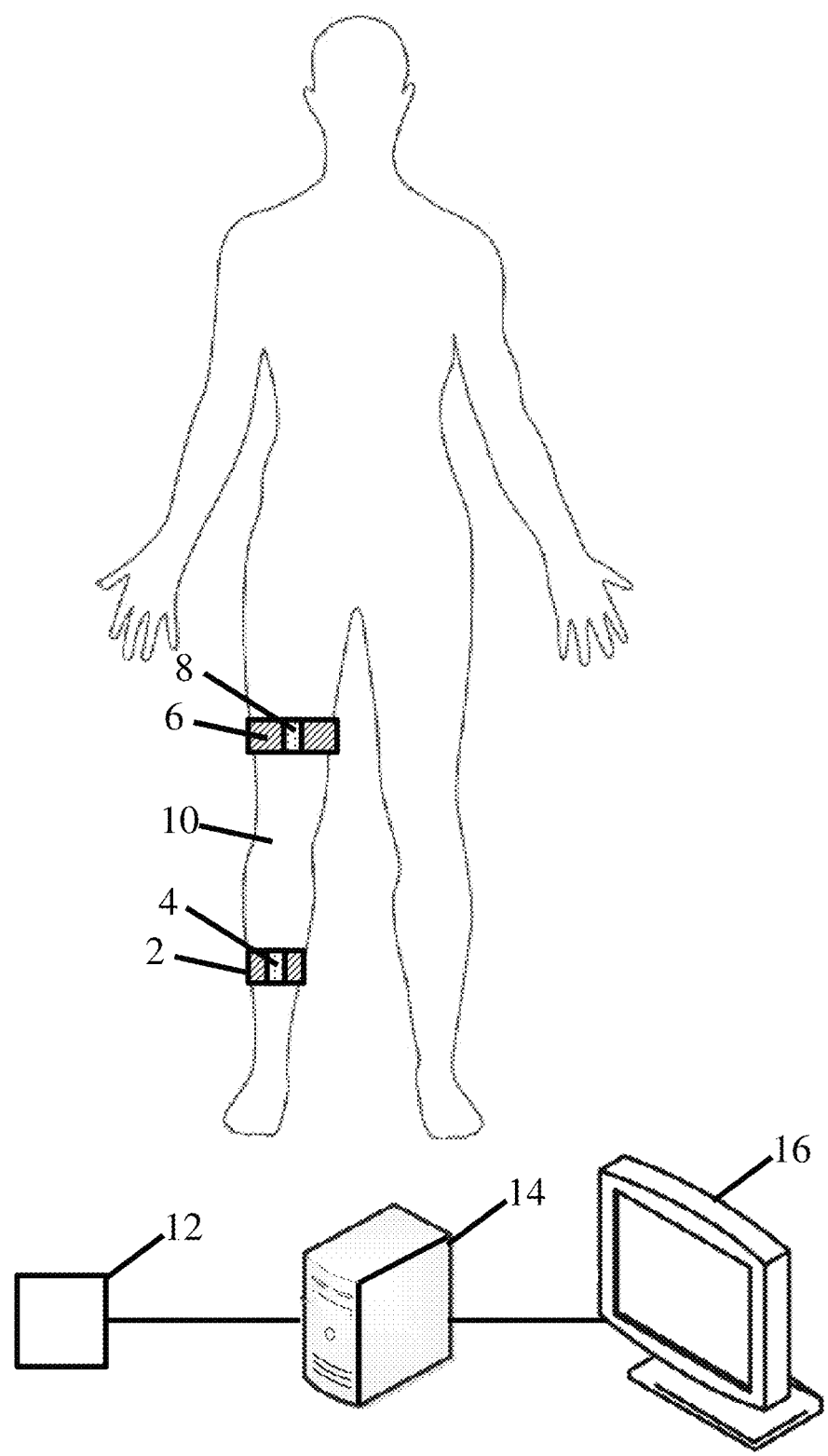
FIG. 1 is a schematic representation of a movement monitoring system used to monitor a subject's knee.

As noted previously, post-operative follow up for various types of joint surgery typically includes periodic return visits of the subject to a clinical environment to meet with the medical team for updates and/or in-home physical therapy visits. Both of these options are costly in terms of both time and money and are in many cases disruptive to the subject's recovery. Therefore, the inventors have recognized that there is a need for meaningful, cost-effective, and in some instances portable, subject movement monitoring solutions. For example, the ability to allow subjects to go about their daily activities with minimal intrusion while allowing medical staff to monitor their recovery progress may save all parties involved a great deal of time and money. Further, such a system may permit monitoring of orthopedic recovery and can help with the identification of subjects that may need more or less care from their medical team to ensure a successful recovery without the above noted office and/or home visits in some instances.

In view of the above, the inventors have recognized the benefits associated with a movement monitoring system that monitors the movement of a desired joint. In one such embodiment, a movement monitoring system may include a first set of sensors attachable to a first body portion on a first side of a joint and a second set of sensors that are attachable to a second body portion on a second side of the joint. Movement of the first and second sets of sensors relative to one another will thus correspond to the relative movement of the associated body portions which may then be used to determine the movement of the corresponding joint within one or more desired anatomic planes.

In some embodiments, after collecting the data sets noted above using the first and second sensor sets associated with the first and second body portions, the data sets may be communicated to any appropriate computing device. The computing device may then determine the relative motion of the first and second body portions with the communicated data sets using appropriate functional relationships detailed further below. Once the relative motion of the two body portions has been determined, movement of the associated joint may also be determined in at least one plane of motion, and in some embodiments multiple planes of motion, using this information. Various types of information related to the joint movement may then be calculated and output in a viewable format to a practitioner or user for evaluation of a subject's recovery as detailed further below.

In one exemplary embodiment of the above noted concepts, a first set of sensors may be attached to a calf or shin on one side of a subject's knee while a second set of sensors may be attached to a subject's thigh on the other opposing side of the knee to measure the accelerations and/or other movement data of these two body portions relative to one another. The sensors may be located on an interior, exterior, front, back, or other appropriate portion of the calf, shin, and/or thigh as the disclosure is not so limited. The resulting first and second data sets associated with the subject's shin and thigh may then be used to determine the motion of these two body portions relative to one another. This relative motion of the two body portions associated with the knee is subsequently used to determine the corresponding movement of the knee in one or more planes such as the sagittal, frontal, and/or transverse movement planes.

Depending on the joint being monitored, the expected activity level of a subject, the typical speeds at which a particular joint is manipulated, the amount of available data storage, and/or how often data is upload, the collected data sets may be collected over a number of different time periods and frequency ranges. For example, data may be collected over a range of time periods including, but not limited to, between 4 hours and 8 hours, 4 hours and 12 hours, 1 day to 1 week, 1 week to 2 weeks, 2 weeks to 6 weeks, 6 weeks to 12 weeks, or any other appropriate time period as the disclosure is not so limited.

Regarding the sampling frequency, in some embodiments, a sampling frequency is sufficiently fast to ensure that movement of the joint is adequately captured while being sufficiently slow enough to provide a desired battery life and data set size. For instance, sampling too fast will lead to increased battery drainage and data sets that are either unmanageable and/or fill the available device memory prior to the completion of a time period being monitored. Consequently, in some embodiments, a sampling frequency of a set of sensors may be greater than or equal to about 20 Hz, 40 Hz, 60 Hz, or any other appropriate frequency. Correspondingly, the sampling frequency may be less than or equal to about 150 Hz, 100 Hz, 80 Hz, 60 Hz, or any other appropriate frequency. Combinations of the above range of frequencies are contemplated including, for example, a sampling rate between or equal to about 20 Hz and 150 Hz. However, sampling frequencies both greater than and less than those noted above are also contemplated as the disclosure is not so limited.

In addition to the above, the particular type of data sets collected to determine the movement of a joint may correspond to any number of different types of acceleration, velocity, and/or orientation information. For example, in one embodiment, the various sets of sensors associated with a joint may sense linear and/or rotational accelerations relative to at least one axis, and in some embodiments, relative to three separate axes. Additionally, in some embodiments, the sets of sensors may sense linear and/or rotational velocities relative to at least one axis and/or three separate axes instead. Further, in yet another embodiment, the sets of sensors may sense orientation, such as a magnetic orientation, relative to one axis and/or three separate axes. However, embodiments in which the sets of sensors sense linear accelerations, rotational velocities, and/or orientations are also contemplated. In one such embodiment, the first and second sets of sensors may both include a triaxial accelerometer, a triaxial gyroscope, and/or a triaxial magnetometer such as may be present in a typical inertial measurement unit (IMU) or other appropriate sensing device. In instances where both linear acceleration, rotational velocities, and/or orientations of two or more body portions are used, the resulting positional data may be combined using a sensor fusion technique such as a complementary or other type of filter as detailed further below.

While several different types of sensors and data for sensing the movements and/or orientations of body portions are described above, it should be understood that any type of sensor capable of measuring a physical quantity that may be used to determine the orientation, movement, and/or relative positioning of the body portions associated with a joint may be used as the current disclosure is not limited in this fashion.

It should be understood that the disclosed movement monitoring systems disclosed herein may be used with any appropriate joint. For example appropriate joints that might be monitored using various combinations of sensors include, but are not limited to, an ankle, a knee, a hip, a wrist, an elbow, a shoulder, and a spine to name a few. In one such embodiment, a first set of sensors may be connectable to a shin of a subject and a second set of sensors may be connectable to the thigh of a subject. In another embodiment, a first set of sensors may be connectable to a subject's sternum, or other portion of their torso, and a second set of sensors may be connectable to a subject's humerus (i.e. their upper arm). In yet another embodiment, two or more sets of sensors may be located proximate next to two or more vertebrae. Further, in some applications, the sensors may be located proximate to two or more non-adjacent vertebrae. It should be understood that any appropriate method of locating the sensors proximate to the desired vertebrae may be used including, for example: sensors integrated into a shirt, vest, compression garment, adhesives, or other wearable structures. Of course while specific types of joints and arrangements of sensors are described above, other methods of attaching the sensors to a body portion as well as the use of sensors with joints other than those noted above are also contemplated.

For the sake of clarity, the embodiments described herein are primarily directed to sensing the motion associated with a knee joint after total knee arthroplasty surgery to assess the postoperative recovery of a subject. However, the presently disclosed systems and methods may be used to monitor the movement of a joint for any number of different reasons including, but not limited to: monitoring of degenerative conditions and diseases such as osteoarthritis, rheumatoid arthritis, degenerative disc disease, and other conditions or diseases for intervention purposes once joint movement is sufficiently impeded relative to nominal joint movement characteristics; assessing athletic abilities and performance of a subject performing various activities and/or participating in a sport; evaluating joint performance, subject movement, and/or physical progress after physical trauma, stroke, or other appropriate conditions; postoperative recovery of a subject as previously described; and/or any other appropriate application as the disclosure is not so limited.

Turning now to the figures, several nonlimiting embodiments are described in further detail in reference to the figures. While specific arrangements and combinations of features are detailed herein, it should be understood that the current disclosure is not limited to only the depicted embodiments. Instead, the current disclosure encompasses any suitable combination of the various features and embodiments described herein as the present disclosure is not limited in this respect.

FIG. 1 depicts a schematic embodiment of a movement monitoring system. The system includes a first sensing device including a first body coupling 2 and a first set of sensors 4 connected to the first body coupling. Similarly the system includes a second sensing device including a second body coupling 6 and a second set of sensors 8 connected to the second body coupling. In the depicted embodiment, the two couplings are worn above and below the knee joint 10. Specifically, the first set of sensors are positioned on a shin or calf of the subject and the second set sensors are positioned on a thigh of the subject. In order to appropriately attach the sensors to the subject's body, it is desirable that the body couplings maintain a position and orientation of the sensors on the associated body portion during use. This may be accomplished in any number of ways. For example, body couplings used to attach one or more sets of sensors to any appropriate body portion, including the above noted thigh and shin or calf, may correspond to elastic straps, tightenable straps, elastic compression garments, a series of tethers, patches attached with adhesives, and/or any other appropriate arrangement capable of attaching the first and second sets of sensors to the associated body portions located on either side of the desired joint. Additionally, the various sets of sensors included in the movement monitoring system may either be embodied as separately attached components or they may be integrated into a single garment or device that is attached to, or donned by, a subject at the same time such that the sensors are located proximate to the desired body portions on opposing sides of the joint being monitored once the garment or device is attached to, or worn by, a subject.

In some embodiments, the first and second sets of sensors, 4 and 8 respectively, may communicate with an associated computing device 14, either directly through a wired connection and/or wirelessly, to upload the sensed data from the body portions they are associated with. However, in other embodiments, a separate docking station 12, such as that shown in FIG. 1 may be used. In such an embodiment, the docking station may include connectors, or wireless communication devices such as a Bluetooth device, that communicate with the first and/or second set of sensors when they are docked with the docking station. In some embodiments, the docking station may also include electrical connectors that recharge the first and/or second sets of sensors when they are docked. While docked with the docking station, the docking station may download, and subsequently upload, acceleration, velocity, and/or orientation data from the first and second set of sensors to the associated computing device through either a wired and/or wireless connection as the disclosure is not so limited. Once the data are uploaded to the computing device, the data may be appropriately processed and analyzed as detailed further below to determine movement of the joint 10. After determining the movement data associated with the joint, appropriate range of motion metrics may be calculated and formatted for viewing and output to an output device 16 as illustrated in the figure.

While a monitor has been depicted in the figure, it should be understood that any appropriate output device including, but not limited to, integrated displays on the movement monitoring system itself, standalone displays, printers, tablets, smart phones, or any other device capable of displaying information to a user may be used as the disclosure is not so limited. Also, while the depicted computing device has been depicted as being separate from the docking station and/or sensors, and has been shown as using a direct connection to the docking station other arrangements are also contemplated. For example, depending on the embodiment, the first and second sets of sensors may be directly connected to, wirelessly connected to, integrated with, or otherwise in communication with the computing device without the need for a docking station. A system where the sensors, computing device, and/or an output device are integrated may enable real time data management and feedback. It is also noted that in embodiments using a docking station, the docking station may be directly connected to, wirelessly connected to, integrated with, or otherwise in communication with the computing device as the disclosure is not so limited. It is also noted that the sensors may be connected with an output device and/or the computing device in any appropriate manner including but not limited to individual connections and a mesh network connection.

Figure 2:
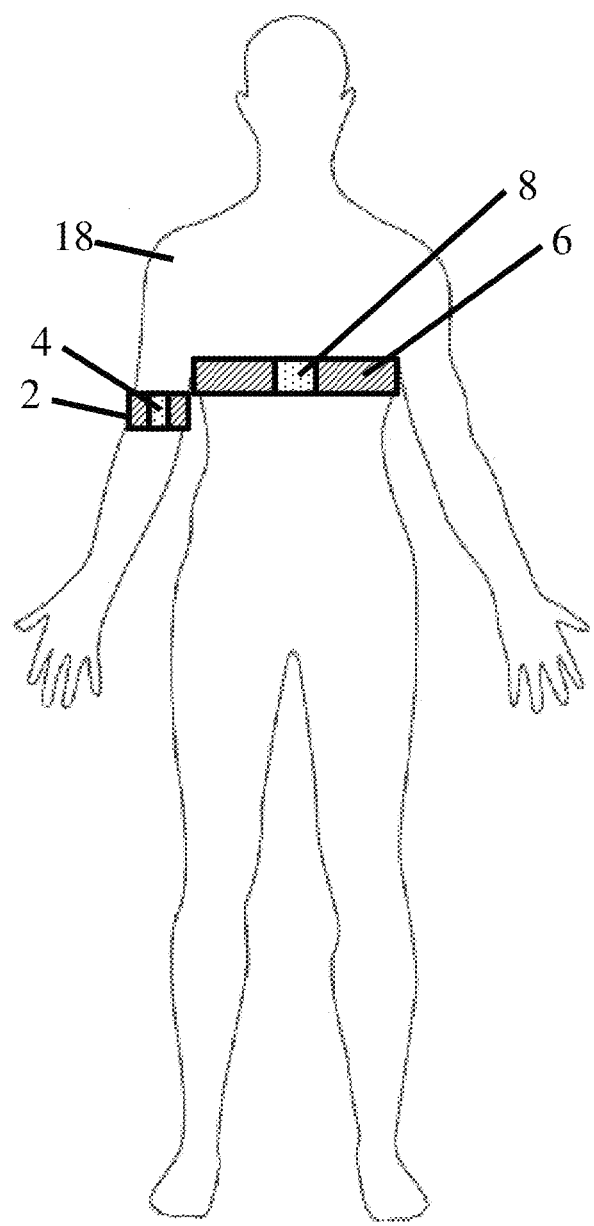
FIG. 2 is a schematic representation of a movement monitoring system used to monitor a subject's shoulder.
Figure 3A:
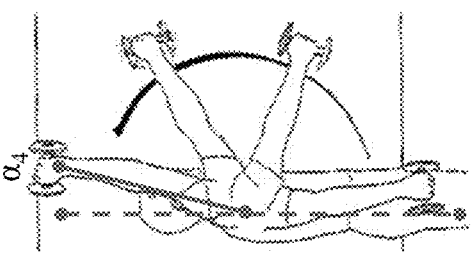
FIG. 3A-3D are schematic representations of angular measurements associated with a subject's shoulder range of motion.
Figure 3B:
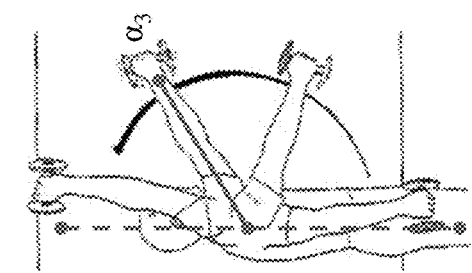
Figure 3C:
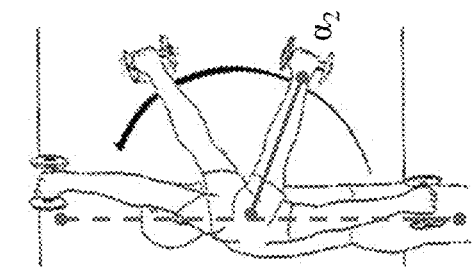
Figure 3D:
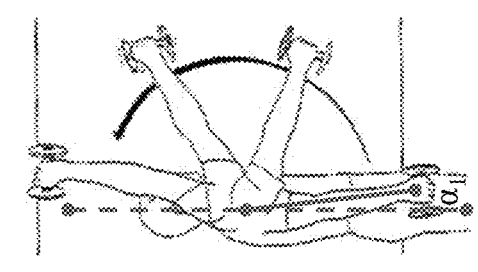

As mentioned previously above, a motion monitoring system as described herein may be used to monitor the motion of any appropriate joint. Consequently, while a knee joint has been described above, other implementations of a motion monitoring system may also be used. For example, in another embodiment depicted in FIG. 2, a motion monitoring system is used to monitor the motion of a shoulder joint 18. Again, the first and second sensing devices include a first body coupling 2 that attaches the first set of sensors to a first body portion associated with the shoulder and a second body coupling 6 that attaches a second set of sensors 8 to a second body portion associated with the shoulder. In this particular embodiment, the first and second body portions correspond to the upper arm and torso (i.e. humerus and sternum) of the subject.

FIGS. 3A-3D depict a schematic of a subject raising their arm from adjacent to the body to over their head. As the subject raises their arm, an angle relative to a plane passing vertically through the subject's body changes from the first angle $\alpha_1$ located adjacent to the body to an angle $\alpha_4$ corresponding to the arm being located over the subject's head. Therefore, in some embodiments, a movement monitoring system may monitor the angle and/or an associated elevation of the shoulder joint associated with such a motion.

Figure 4:
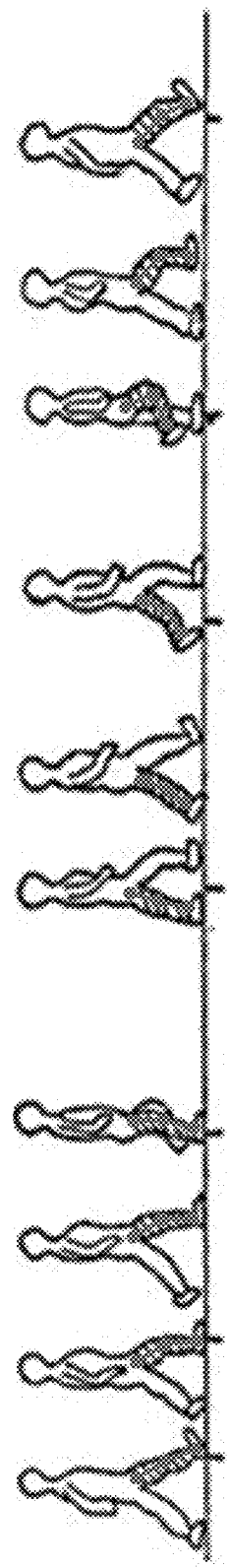
FIG. 4 is a schematic representation of the relative positions of the different portions of a subject's leg while in different stances during a walking gait cycle.

FIG. 4 presents the relative angular positions of a subject's leg when in different phases during a walking gait cycle. For example, the illustrated walking gait cycle illustrates various portions such as the stance and swing phases which include events such as heel strike, quarter-stance, mid-stance, heel off, toe off, and mid-swing prior to returning to heel strike. Movements such as these have very specific movement signatures associated with them that can be identified by looking at the movements of various joints such as the knees and ankles. Consequently, by looking at the movement data versus time of a joint, it is possible to determine what type of activity an individual was engaging in. For example, events that might be identified include, but are not limited to, walking, running, sitting, squatting, overhead reaching, and arm swing during gait. More specifically, in some embodiments, it is possible to determine specific ranges and patterns of motion for the above-mentioned joints within one or more anatomic planes. Once identified, motion profiles or ranges of motion from the movements may then be compared to motion profiles or ranges of motion from the same type of movement captured at different time points to evaluate the recovery of a subject.

Figure 5:
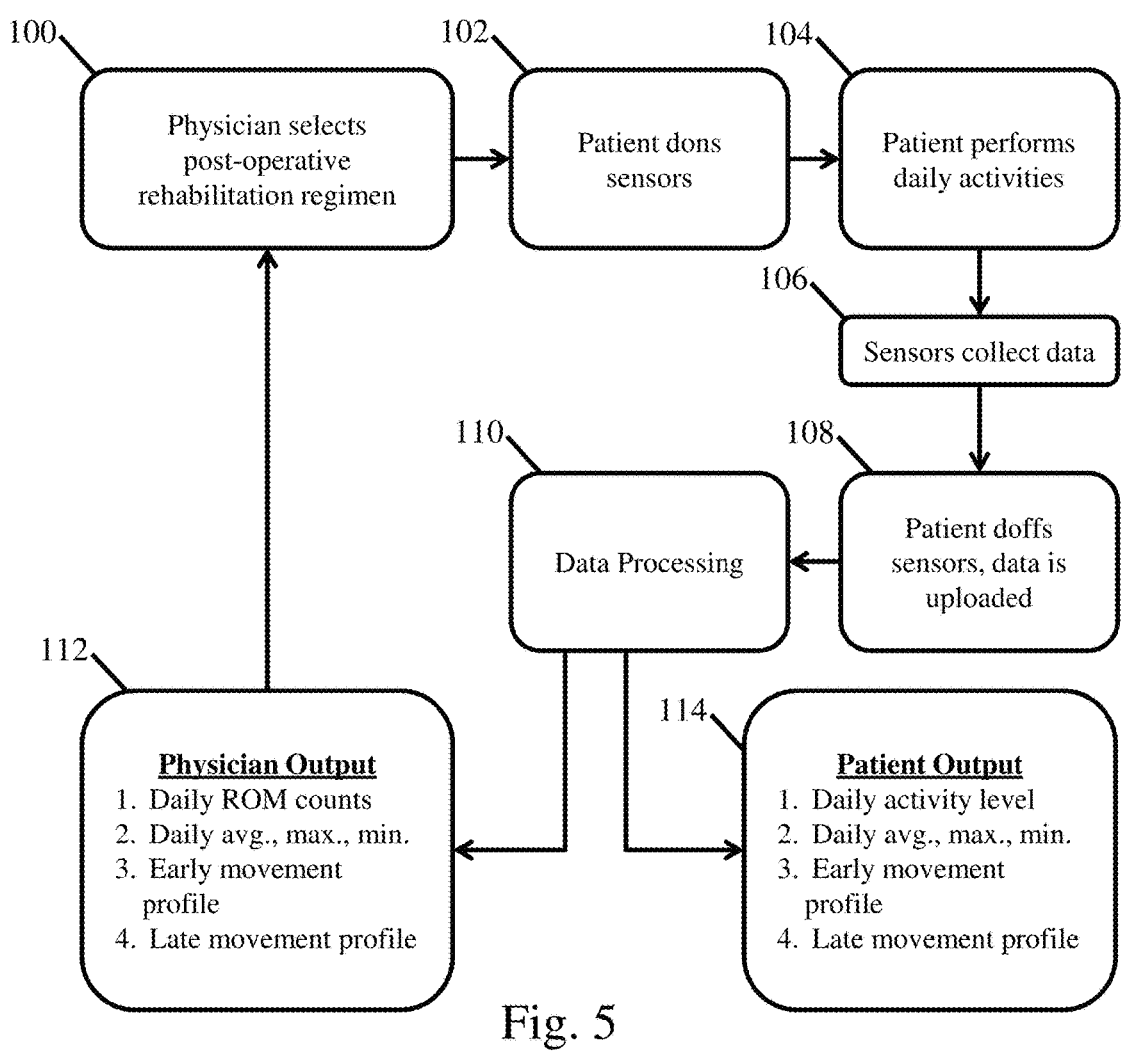
FIG. 5 is a flow diagram detailing the use of a movement monitoring system during a rehabilitation process.

FIG. 5 is a flow diagram detailing the use of a movement monitoring system during a rehabilitation process. At 100 a physician, or other medical personnel, selects a post-operative rehabilitation regime for a subject recovering from a joint surgery. As noted previously, this might correspond to a particular physical therapy regimen and/or other appropriate types of post-surgical recovery techniques. As part of this rehabilitation regimen, the physician may prescribe the use of a movement monitoring system, such as those described herein, to provide feedback related to the subject's recovery over time. During use, the subject dons the first and second sensors associated with the movement monitoring system at 102. For example, the subject may attach the first set of sensors to a first body portion associated with a joint in a desired orientation and location. The subject may then attach the second set of sensors to a second body portion located on an opposing side of the joint in a desired orientation and location. The subject may then perform their normal daily activities during the recovery period, including any prescribed physical therapy, see 104. The first and second sets of sensors collect acceleration, velocity, and/or orientation data associated with movement of the body portions at a desired frequency while the sensors are worn. In some embodiments, the first and second sensors may operate for a set duration, whenever they are worn, and/or when they are activated by a user as the disclosure is not limited to any particular sampling rate or period. At 108, the subject doffs, i.e. removes, the first and second sets of sensors from their associated body portions. The data recorded by the first and second sets of sensors is then uploaded to a corresponding computing device as described previously. The uploaded data is then subjected to various forms of data processing at 110 to determine the movements the monitored joint has undergone throughout the monitoring period. The particular relationships and processes performed during data processing are described further below.

After appropriately processing the movement data, various metrics related to movement of the joint are output for viewing by a subject and/or a physician or other medical personal. As noted previously, the types of outputs may include graphics, statistics, comparative curves, spreadsheets, and/or other appropriate methods of displaying the desired performance metrics. Additionally, the outputs may either be output to a display and/or printed out as a hardcopy for viewing by the subject and/or medical personal. Exemplary types of metrics that might be output for a medical personnel and/or a subject include, but are not limited to: daily activity level; daily average, maximum, and/or minimum positions or motions of the joint; a characteristic movement profile of the joint from an earlier time period and a later time period during a session (e.g. earlier and/or later within a day); daily range of motion counts; and/or any other desirable metric that may be useful and/or desirable for viewing.

After the metrics from a monitored joint have been output for viewing, the subject, a physician, or other medical personal, may review a subject's recovery progress daily, every other day, weekly, or on any other desired time line. Further, when viewing the metrics for a joint being monitored, the subject, a physician, or other medical personal overseeing that subject's recovery, may evaluate how rehabilitation is progressing. For example, depending on how a subject's recovery is progressing, a different modified rehabilitation regimen may be implemented, the prescribed rehabilitation regimen may be continued, or further rehabilitation may not be necessary while monitoring may or may not continue to ensure that recovery is complete. Of course, this process may be done iteratively over the entire course of a subject's recovery.

Figure 6:
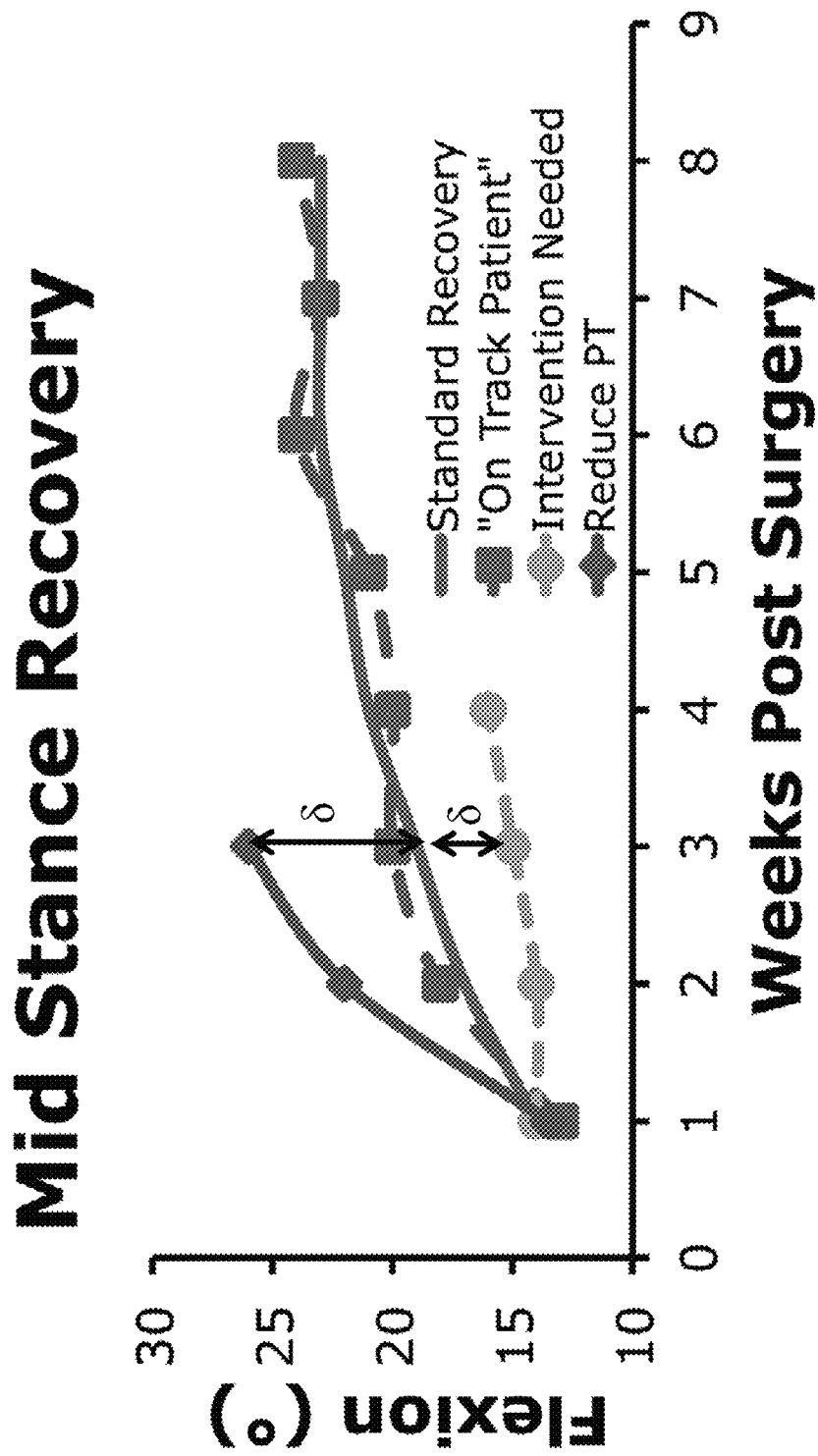
FIG. 6 is a graph of exemplary measured recovery curves versus a standard recovery curve.

As part of the data processing and output of information to a medical practitioner described above, in some embodiments, it may be desirable for a movement monitoring system to help identify subjects in need of intervention including, but not limited to, surgical, physical therapy, musculoskeletal manipulation, and/or any other appropriate type of intervention. For example, FIG. 6 depicts one embodiment of a standard recovery curve for a particular type of surgery. Separately, a subject that is experiencing an "on track" recovery is depicted where a movement metric, such as a range of motion movement metric, which in this case corresponds to a mid-stance flexion of a knee joint, fairly closely tracks the standard recovery curve over the depicted recovery duration of 8 weeks. In contrast, a subject in need of intervention is also depicted in the figure where the joint movement metric after surgery diverges from the standard recovery curve by an amount δ. Additionally, as shown in the figure, a subject that has experienced an accelerated recovery with a movement metric that is greater than the expected standard recovery curve may not need to continue the current regimen of physical therapy, and depending on their particular case, may either have the amount or type of physical therapy reduced or ended.

In view of the above, in some embodiments, a movement monitoring system may compare one or more movement metrics of a joint being monitored for a subject to one or more standard movement metrics of the joint. This may either be normal movement metrics of the joint; expected or standard movement metrics of the joint versus time after surgery, trauma, or other event as illustrated in the figure; and/or any other appropriate movement metric for the joint being monitored. Thus, a system may be used to determine if a condition, such as osteoarthritis, has progressed to a point where intervention is warranted, if a subject is progressing appropriately during a recovery period, and/or for any other appropriate application. For example, when a difference δ between the detected movement metric of the joint and the standard movement metric of the joint, for either normal use or during a recovery period, is greater than a predetermined threshold, the movement monitoring system may determine that intervention for that particular subject is needed and output this determination to the medical practitioner in any appropriate way. In one such embodiment, when the movement metric is greater than the standard metric by a preset threshold, the existing interventions, such as physical therapy, may be reduced or ended. Correspondingly, when the movement metric is less than the standard metric by a preset threshold, increased and/or new types of interventions may be implemented to aid the subject's recovery and bring the subject's movement metric towards the standard movement metric.

It should be understood that the specific thresholds and standard movement metrics will vary depending on the particular joints being monitored and the specific application the movement monitoring system is being used for. Further, depending on the particular application, the above noted threshold may be a constant value or the threshold may change versus an appropriate application dependent variable (e.g. the threshold may be a function of time after surgery, trauma, or other event). Further, in some embodiments, multiple thresholds may be used by the movement monitoring system to determine whether or not different types of interventions might be implemented for a particular subject. For example, a movement monitoring system may determine that a first type of intervention may be used when the difference between the detected and standard movement metrics exceed a first threshold and that a second different type of intervention may be used when the difference between the detected and standard movement metrics exceed a second larger threshold. These different types of suggested interventions may then be output to the medical practitioner as noted previously.

Figure 7:
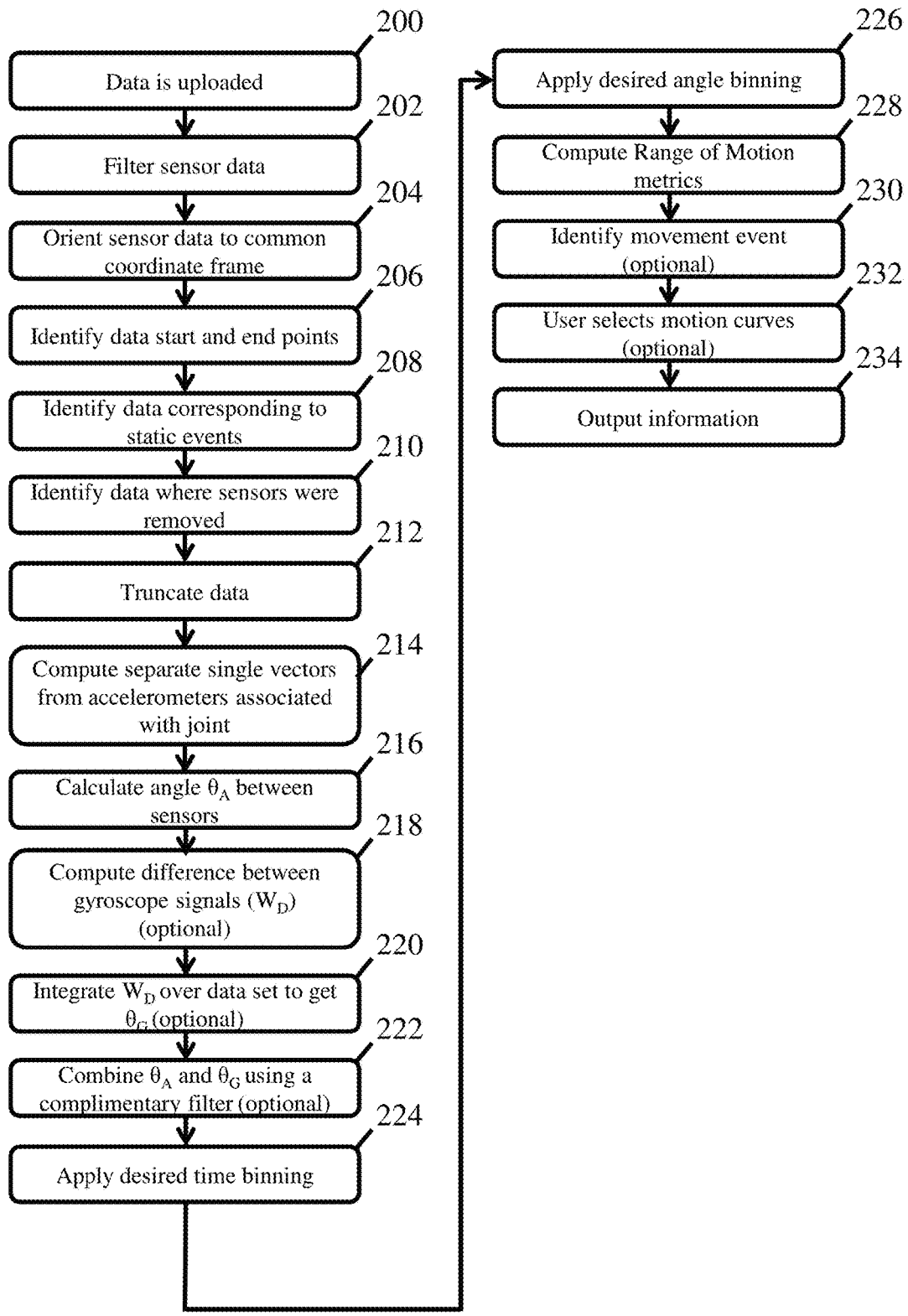
FIG. 7 is a flow diagram detailing data processing and output from a movement monitoring system.

FIG. 7 presents one possible embodiment of a data processing method for determining the movement of a joint using acceleration data from two associated body portions located on opposing sides of a joint. At 200, first and second data sets are uploaded to a computing device as noted previously using any appropriate upload method. The uploaded data may then be time synced and subjected to any number of noise reduction filters, and delivered as the input to an algorithm that outputs clinically relevant parameters related to the joint at 202. For example, in one embodiment, a low pass filter with a desired cutoff frequency, such as a Butterworth filter may be used. Appropriate ranges for a cutoff frequency are between or equal to 1 Hz and 20 Hz. However, it should be understood that other types of filters and frequency ranges may also be used, as the disclosure is not so limited.

Due to the first and second sets of sensors being put on by a subject, the sensors may not always be oriented properly and/or in some instances, a subject may swap the locations of the sensors. For example, a subject may position the sensor in an upside down orientation and/or they may wear a sensor intended for one body portion on a different body portion. If these events were to occur, in some embodiments, it may be desirable for the sensed movement data to still be useful for monitoring movement of the joint. Therefore, in some instances, a computing device may orient the first and second sensor data sets to a common coordinate frame as illustrated at 204. While this may be accomplished in any number of ways, in one embodiment, the associated computing device may identify an orientation and location of the sets of sensors by computing a rotation matrix between the sets of sensors during an initial stationary period (i.e. when the sensors are worn, but the subject is stationary) identified in the data sets. In one embodiment, data sets during this initial static stationary pose can be compared to known acceleration and/or movement values for a correctly placed sensor. The computing device associated with the system can then identify differences between the actual placement of the sensors and the expected data values for a correctly placed sensor. A corresponding rotation matrix can be computed from the difference between the actual and theoretically correctly placed sensor. If a sensor is identified as being in the wrong orientation, the associated data set is rotated to the other sensor's coordinate frame using the appropriate rotation matrix. Similarly, if it is determined that the sensors have been worn on the incorrect body portions, the data sets may then be reversed for use in subsequent analysis steps.

At 206-210, the computing device identifies where the data sets start and end as well as identifying portions of the data sets corresponding to static events (i.e. when a subject is relatively still while wearing the sensors) and paused portions of the data sets when a subject has removed the sensor sets (e.g. a person might remove the sensors during swimming). Depending on the embodiment, the computing device may differentiate between data corresponding to static events and when the sensors are removed using an acceleration or joint movement threshold. For example, acceleration values that are constant within $\pm 0.01$ m/s$^2$, $\pm 0.05$ m/s$^2$ or any other desirable threshold over a time period greater than about 30 sec to 1 min may indicate that the sensors have been removed. Similarly, movements that are equal to or less than 0.5°, 1°, or any other desirable threshold observed over a similar time period may also indicate that the sensors have been removed as opposed to the small but measurable movement expected from a person remaining in a stationary position. In one such embodiment, a threshold for determining sensor removal are movements that are less than or equal to 1° over a period of time that is greater than or equal to thirty seconds. However, other possible thresholds and time periods both greater than and less than those noted above may also be used, as the disclosure is not so limited. After identifying the above noted portions of the data set, the algorithm implemented on the computing device may then truncate the data to remove data prior to the start point and after the endpoint as well as removing data associated with time increments when the sensors were removed at 212.

Once the data sets have been appropriately pre-processed, the computing device may then proceed with analyzing the data to determine a range of motion of a joint using the relative movement of the body portions recorded in the acceleration data as detailed further below.

In one embodiment, the acceleration data associated with each sensor set is converted to a single vector. The angle between the newly created vectors from the sensor sets is then calculated using $\theta = a\cos((v1 \cdot v2)/(|v1||v2|))$. Of course such a calculation may be expanded to increased levels of complexity by creating more than a single vector (i.e. two, three vectors) to compute three-dimensional angles. While a particular calculation method has been described above, it should be understood that any appropriate method of using the acceleration data to determine the angles between the different moving body portions may be used as the disclosure is not so limited.

In some embodiments, it may be desirable to provide additional accuracy for a measured joint angle. In such an embodiment, the movement data may include both linear acceleration and rotational velocities as noted previously. The calculated angles associated with the linear acceleration portions of the data may be determined as noted above. Additionally, the differences between the two rotational data sets $W_D$, such as between two triaxial gyroscopes signals, may be determined at 218 to provide the rotational velocities experienced by a joint during the monitoring period. $W_D$ may then be integrated over the total data set for the sampled time increment to determine an angle data set $\theta_G$ at 220. The angle data sets $\theta_A$ and $\theta_G$ may be combined in any appropriate manner using sensor fusion using any number of combinatory filters including but not limited to a complimentary filter or a Kalman filter. For example, in one embodiment, and as shown at 222, the data sets may be combined using a complementary filter to determine a combined total angle data set $\theta_{Total}$ according to the relationship below.

$$\theta_{Total_n} = \lambda \theta_{A_n} + (1-\lambda)(\theta_{Total_{n-1}} + (\theta_{G_n} - \theta_{G_{n-1}}))$$

Depending on the particular application, $\lambda$ may either be constant if the movements of a joint are well known, or they may be adaptive if the movements are not well known which may increase the accuracy at the expense of increasing the complexity of the model. For example, in one embodiment implementing an adaptive complementary filter, $\lambda$ may be speed dependent such that portions of the data including data variations above a threshold velocity are primarily calculated using the gyroscope data and portions of the data including data variations below a threshold velocity are primarily calculated using the accelerometer data. This may be of use due to accelerometers providing more accurate angular data at lower velocity ranges and gyroscopes providing more accurate angular data at higher velocity ranges. While any appropriate threshold velocity cut off may be used, in one embodiment, the threshold velocity may be between or equal to about 135°/sec and 180°/sec.

After determining the final angular data set associated with movement of the joint, the computing device may then apply a desired time bin length and/or angle bin size to the data at 224 and 226. For instance, data collected from a subject who has received a knee replacement, or other joint surgery, can be collated into bins to identify the percentage of time that a subject might spend in any given flexion angle; average gait parameters; or maximum gait parameters. However, regardless of any particular application, appropriate time bins may have lengths between or equal to about 0.5 sec and 1 sec, 1 sec and 5 sec, 5 sec and 30 sec, and/or any other desirable time length. Similarly angle bins between or equal to 1° to 5°, 5° to 10°, or any other appropriate angular range may be used. Further the associated range of angles that are binned may be any appropriate range associated with a particular joint including, but not limited to, 0° to 90° and 0° to 180°.

After appropriately binning the data, the computing device may subsequently determine any number of a range of motion metrics at 228. These metrics may include, but are not limited to: a total number of movement counts associated with a particular joint position (i.e. the number of time bins associated with each angle bin); the percent of total time spent in particular joint positions (i.e. the percent time the angle data is in each angle bin); discrete movement counts (i.e. the number of non-consecutive time bins in each angle bin); percent of discrete movement counts (i.e. the percent of non-consecutive time bins in each angle bin); daily range of motion averages, minimums, maximums, and maximum angle bins with at least 10 counts in them.

In addition to the above, in some instances it may be desirable to provide samples of a particular type of movement curve for a joint such as a Paul curve corresponding to the walking gait cycle of an individual during one or more portions of a monitoring period. In such an embodiment, the computing device may identify a series of captured movements that indicate the desired type of movement using either a series of identified inflection points, or other appropriate metric at 230, during one or more time periods such as towards the beginning and end of the monitoring period (e.g. within an hour of the start and end of the data set). Further, in some instances, a user may select a particular motion curve from within the identified movement events as being representative of a desired motion curve at 232.

After determining the appropriate metrics, and/or identifying a desired motion curve, the information is output for viewing by a user such as a patient and/or medical personnel at 234 in any appropriate manner as detailed previously.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, a tablet computer, a processor and memory embedded in a movement monitoring system.

Additionally, a computing device may be embedded in a device not generally regarded as a computing device but with suitable processing capabilities, including a Personal Digital Assistant (PDA), a smart phone, or any other suitable portable or fixed electronic device.

Also, a computing device may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Such computing devices may be interconnected by one or more networks in any suitable form, including as a body area network, a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the disclosed embodiments may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a non-transitory computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Example: Static and Removed Sensor Comparison

Figure 9:
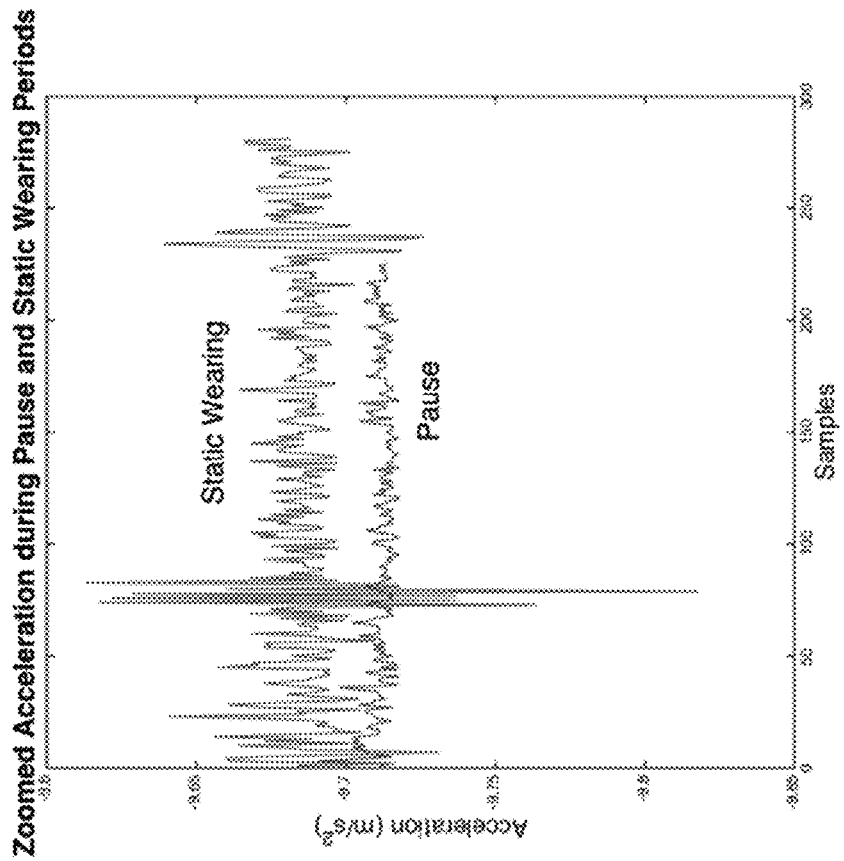
FIG. 9 is a graph comparing acceleration data corresponding to a paused time period and a static time period.
Figure 8:
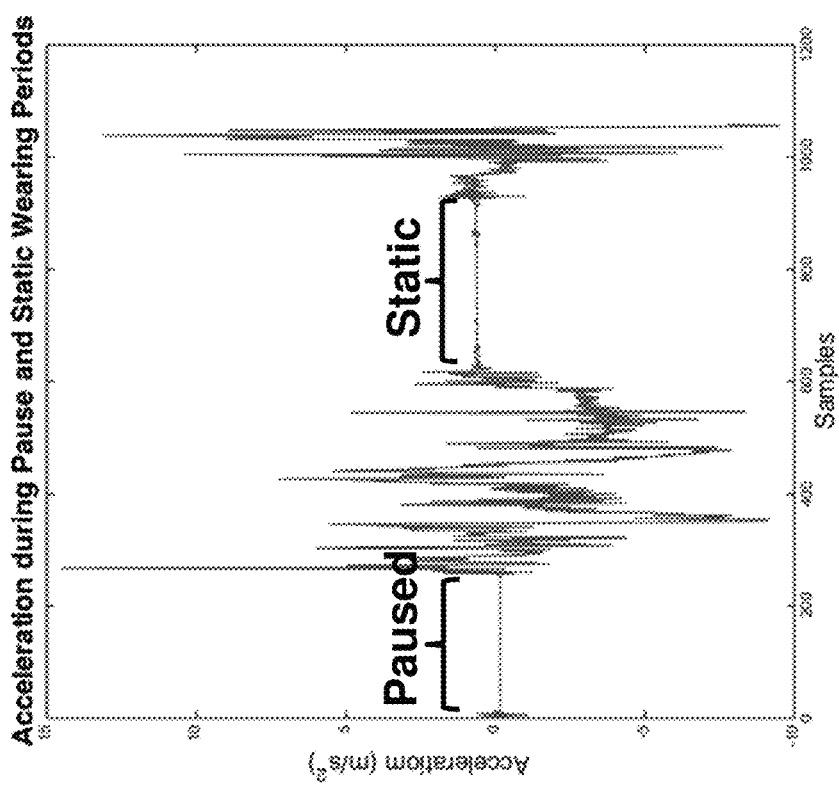
FIG. 8 is a graph presenting acceleration data including data measured during a paused time period when the sensors are not worn and during a static time period when a subject remains stationary.

FIGS. 8 and 9 show comparisons of data where the sensors are not worn, or are paused, and instances where a subject is in a static position. As expected, the static position data of a subject shows a significantly larger signal variation over time than the data associated with sensors that are not worn. Consequently, this confirms that thresholding is an appropriate method to differentiate between these two types of data.

Example: Knee Monitoring Output

Figure 10:
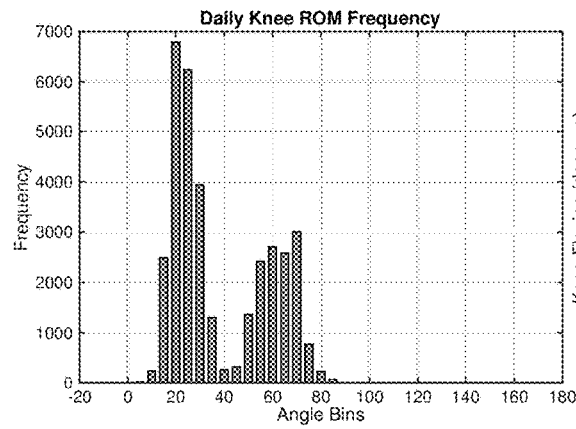
FIG. 10 is a graph presenting knee range of motion data binned in 5° increments.
Figure 11:
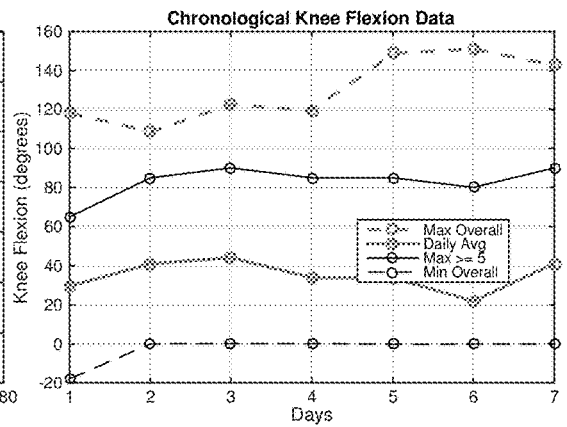
FIG. 11 is a graph comparing various types of knee motion over sequential days.
Figure 12:
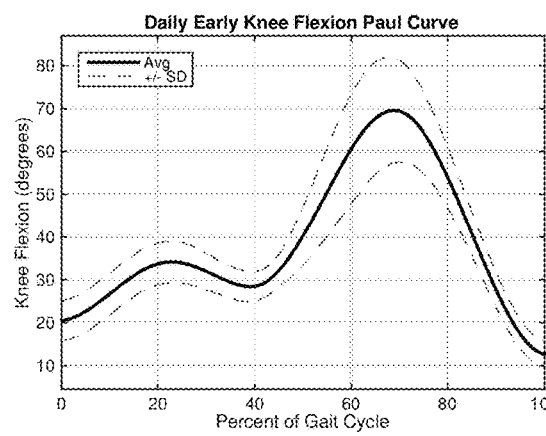
FIG. 12 is a graph of a knee flexion Paul curve taken during an early portion of a day.
Figure 13:
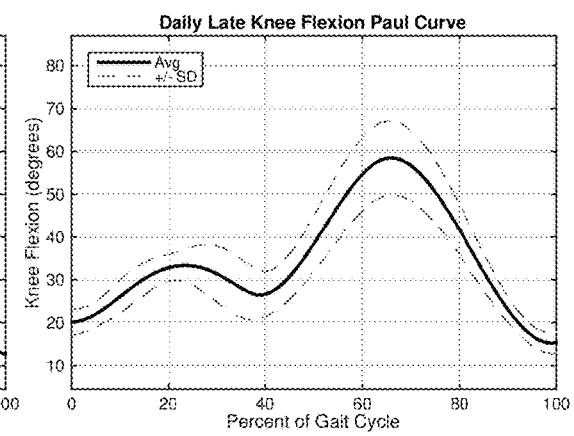
FIG. 13 is a graph of a knee flexion Paul curve taken during a late portion of a day.

FIGS. 10-13 are examples of what might be displayed to medical personnel for a subject recovering from knee surgery. For example, FIG. 10 presents the total counts associated with each angular position of a subject's knee during an 8 hour long monitoring period. FIG. 11 shows the maximum, average, maximum with at least 5 counts, and the minimum angular position of the subject's knee over a week. Additionally, FIGS. 12 and 13 present Paul Curves from earlier in the day and later in the day. The reduced movement of the knee in the Paul Curve from later in the day may indicate that either the subject's knee is stiffer at that time or the subject has fatigued. Again this information may be used to both evaluate and tailor the physical therapy regimen that the subject is prescribed.

Example: Shoulder Monitoring Output

Figure 14:
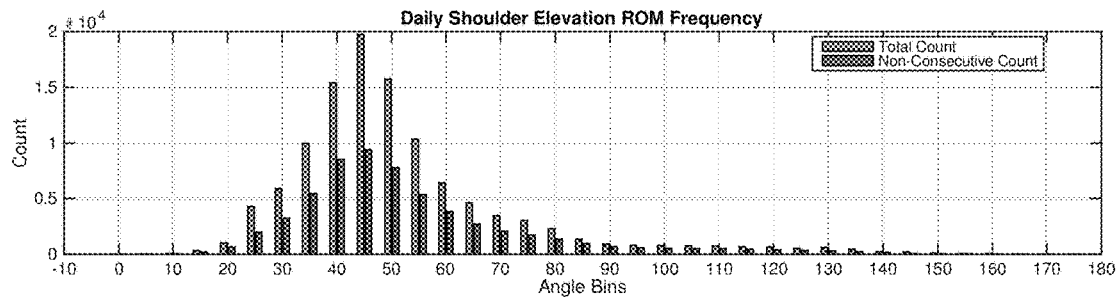
FIG. 14 is a graph presenting shoulder elevation range of motion data binned in 5° increments.
Figure 15:
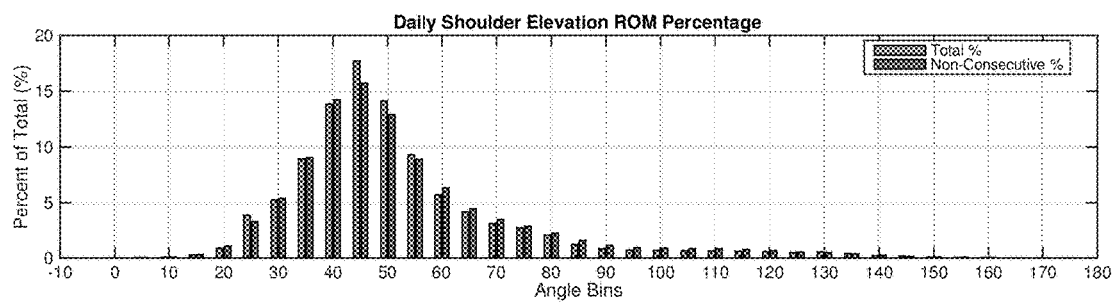
FIG. 15 is a graph presenting shoulder elevation range of motion data binned in 5° increments as a percentage of measured positions during a day.
Figure 16:
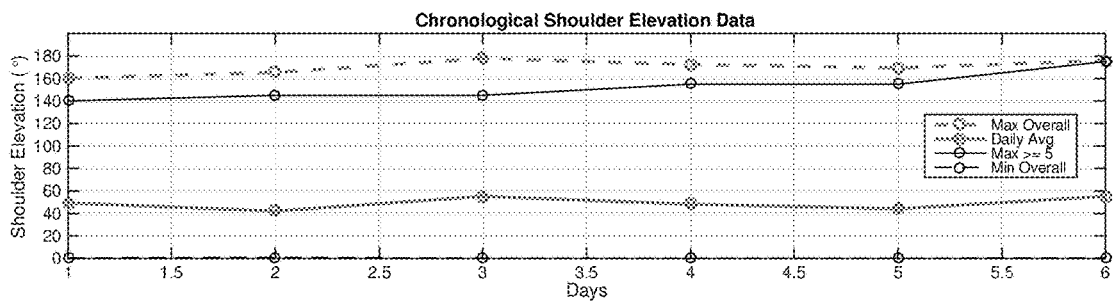
FIG. 16 is a graph comparing various types of shoulder elevation range of motion data over sequential days.

FIGS. 14-16 present exemplary metrics for a subject recovering from shoulder surgery. Similar to the above, FIGS. 14 and 15 show the counts and percentages of time that the subject's shoulder was in a particular angular position. FIG. 16 also shows the maximum, average, maximum with at least 5 counts, and the minimum angular position of the subject's shoulder over 6 days.

Example: Subject Trials

A study was conducted including seventeen patients undergoing total knee arthroplasty (TKA) and 10 healthy control subjects. The patients included 10 men and 7 women with an average age of 64.9±6.4 years. The control subjects included 5 men and 5 women with an average age of 49.7±18.5 years. The patients and control subjects each wore two IMU sensors with one located on the thigh (superior to the femoral lateral epicondyle) and one on the shank (inferomedial to the tibial tuberosity) as previously described herein. Both the patients and control subjects donned the sensors upon waking and removed them prior to sleeping daily for the study duration. Patients wore the sensors on their affected leg for one week preoperatively and postoperatively for approximately six weeks immediately after undergoing the TKA procedure. Control subjects wore IMUs on their dominant leg for one week. It should be noted that the patients were selected from a single surgeon's consecutive caseload.

During the noted monitoring periods, the sensors were temporally synced with each other via local area network (LAN) and captured 9 degree of freedom (DOF) inertial data at 20 Hz (3 axes each of linear acceleration—range: ±6 g, angular velocity—range: ±2000°/s, and magnetic field strength—range: ±6 G). Battery life allowed captures of at least twelve continuous hours of movement data before recharging. Internal data storage permitted greater than 60 consecutive collection days. Data were uploaded to a computing device from the sensors at each study segment termination: 1-week control assessment, 1-week patient preoperative assessment, and 6-week patient postoperative assessment.

While all of the captured data was analyzed for the different study segments, the primary outcomes were measures regarding the first five over-ground strides in the early/latter half of each day. Additionally, daily metrics that were calculated included curves of gait flexion in early/late halves of the day, average daily flexion, and maximum daily flexion. Daily metrics were averaged weekly and the final outcome metrics were provided as weekly averages.

The collected data allowed for the evaluation of knee flexion during the entire gait cycle throughout the day including heel strike, stance, toe off, and swing phases for example. As illustrated by the data in Table 1 below, patients' peak stance flexion during the early portion of the day was reduced preoperatively compared to the control subjects. Weeks 1 and 2 postop patient peak stance flexion in EP was also significantly reduced below both patient preoperative and control levels. However, over weeks 3-6, patients' peak stance flexion improved and was equal to the controls' peak stance flexion. Similar to peak stance flexion during the early portion of the day, peak swing flexion was reduced for patients preoperatively compared to the controls and was further reduced during the first two weeks after undergoing the TKA procedure. However, peak swing flexion for the patients remained less than preoperative levels for the first two weeks, and remained less than controls for the entire study duration.

TABLE 1

|  | Patient (P) | | Control (C) | |
| --- | --- | --- | --- | --- |
|  | Stance | Swing | Stance | Swing |
| Preop | 14° ± 2° | 38° ± 5° | 19° ± 4° | 53° ± 7° |
| Week 1 | 12° ± 3° | 27° ± 6° |  |  |
| Week 2 | 14° ± 3° | 32° ± 8° |  |  |
| Week 3 | 17° ± 3° | 37° ± 7° |  |  |
| Week 4 | 18° ± 3° | 38° ± 7° |  |  |
| Week 5 | 18° ± 2° | 39° ± 7° |  |  |
| Week 6 | 19° ± 2° | 43° ± 12° |  |  |

In contrast to earlier portions of the day, patient gait flexion in the latter portion of the day was reduced preoperatively for the entire gait cycle. However, during later portions of the day, postoperative patient stance flexion was less than preoperative levels and the controls during week 1. Stance flexion then equaled preoperative values by week 2, and surpassed preoperative levels by week 3, but persisted below controls for the duration of the study, see Table 2 below. Flexion during swing during the later portions of the day followed a similar pattern to swing described above during the early part of the day.

TABLE 2

|  | Patient (P) | | Control (C) | |
| --- | --- | --- | --- | --- |
|  | Stance | Swing | Stance | Swing |
| Preop | 15° ± 2° | 40° ± 4° | 24° ± 4° | 62° ± 7° |
| Week 1 | 14° ± 4° | 33° ± 7° |  |  |
| Week 2 | 18° ± 4° | 36° ± 9° |  |  |
| Week 3 | 19° ± 4° | 39° ± 9° |  |  |
| Week 4 | 19° ± 3° | 41° ± 8° |  |  |
| Week 5 | 19° ± 3° | 42° ± 6° |  |  |
| Week 6 | 19° ± 4° | 42° ± 9° |  |  |

It should be noted that the measured movement characteristics of the control subjects in this study are well aligned with established gait standards including stance and swing flexion of healthy individuals indicating that the described sensors and methods are accurate. Further, the study verifies that it is possible to easily, cheaply, and quantitatively monitor physical progress in TKA subjects continuously rather than relying on discrete, idealized clinic/laboratory data points. Additionally, while the study was conducted on sagittal plane knee motion due the to prevalence of TKA surgery and analysis simplicity, the disclosed devices and process may be easily adapted for monitoring other planes of motion (frontal/transverse) as well as for use with other joints.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A movement monitoring system comprising:
   a first set of sensors attachable to a first body portion associated with a first side of a joint;
   a second set of sensors attachable to a second body portion associated with a second side of the joint, wherein the first set of sensors sense at least one selected from the group of linear acceleration, rotational velocity, and orientation of the first body portion and the second set of sensors sense at least one selected from the group of linear acceleration, rotational velocity, and orientation of the second body portion; and
   at least one processor configured to:
      determine a movement metric for the joint of a subject with a first data set from the first set of sensors and a second data set from the second set of sensors;
      determine a difference between the determined movement metric and a standard movement metric;
      determine if intervention is needed for the subject based at least in part on the difference between the determined movement metric and the standard movement metric; and output an indication of whether or not intervention for the subject is needed.

2. The movement monitoring system of claim 1, wherein the joint is a knee.

3. The movement monitoring system of claim 1, wherein the joint is a shoulder.

4. The movement monitoring system of claim 1, wherein the first set of sensors and the second set of sensors sense linear accelerations relative to at least one axis.

5. The movement monitoring system of claim 4, wherein the first set of sensors and the second set of sensors sense linear accelerations relative to three axes.

6. The movement monitoring system of claim 1, wherein the first set of sensors and the second set of sensors sense rotational velocities relative to at least one axis.

7. The movement monitoring system of claim 6, wherein the first set of sensors and the second set of sensors sense rotational velocities relative to three axes.

8. The movement monitoring system of claim 1, wherein at least one of the first set of sensors and the second set of sensors include at least one of a triaxial accelerometer, a triaxial gyroscope, and a triaxial magnetometer.

9. The movement monitoring system of claim 1, further comprising a docking station that is connectable with the first set of sensors and the second set of sensors.

10. The movement monitoring system of claim 9, wherein the docking station is configured to download sensed acceleration, velocity, and magnetic orientation data from the first set of sensors and the second set sensors and upload the sensed acceleration, velocity, and magnetic orientation data to a computing device.

11. The movement monitoring system of claim 10, wherein the computing device is remotely located from the docking station.

12. The movement monitoring system of claim 1, wherein the first set of sensors sense a magnetic orientation of the first body portion and the second set of sensors sense a magnetic orientation of the second body portion.

13. The movement monitoring system of claim 1, wherein the at least one processor is configured to:
determine relative motion of the first body portion and the second body portion using the first data set and the second data set;
determine movement of the joint based on the relative motion of the first body portion and the second body portion; and
determine the movement metric of the joint using the determined movement of the joint.

14. The movement monitoring system of claim 1, wherein the standard movement metric is a function of time.

15. The movement monitoring system of claim 1, wherein the at least one processor is configured to determine that a first intervention is needed if the difference between the determined movement metric and the standard movement metric exceeds a first threshold and to determine that a second intervention is needed if the difference between the determined movement metric and the standard movement metric exceeds a second threshold.

16. A movement monitoring system comprising:
a first set of sensors attachable to a first body portion associated with a first side of a joint;
a second set of sensors attachable to a second body portion associated with a second side of the joint, wherein the first set of sensors sense at least one selected from the group of linear acceleration, rotational velocity, and orientation of the first body portion and the second set of sensors sense at least one selected from the group of linear acceleration, rotational velocity, and orientation of the second body portion; and
at least one processor configured to determine movement of the first body portion relative to the second body portion, wherein above a threshold angular velocity the relative movement is determined primarily with first data from the first and second sets of sensors, and wherein below the threshold angular velocity the relative movement is determined primarily with second data from the first and second sets of sensors.

17. The movement monitoring system of claim 16, wherein the at least one processor is further configured to determine the relative movement of the first and second body portions with sensor fusion to combine the first and second data.

18. The movement monitoring system of claim 16, wherein the first data is rotational velocity data from the first and second sets of sensors, and wherein the second data is linear acceleration data from the first and second sets of sensors.

19. The movement monitoring system of claim 16, wherein the at least one processor is further configured to:
determine a movement metric for the joint with the determined relative movement of the first and second body portions;
determine a difference between the determined movement metric and a standard movement metric; and
determine if intervention is needed for a subject based at least in part on the difference between the determined movement metric and the standard movement metric.

20. The movement monitoring system of claim 19, wherein the at least one processor is further configured to output an indication of whether or not intervention for the subject is needed.

21. The movement monitoring system of claim 19, wherein the standard movement metric is a function of time.

22. The movement monitoring system of claim 19, wherein the at least one processor is configured to determine that a first intervention is needed if the difference between the determined movement metric and the standard movement metric exceeds a first threshold and to determine that a second intervention is needed if the difference between the determined movement metric and the standard movement metric exceeds a second threshold.

23. A movement monitoring system comprising:
a first set of sensors attachable to a first body portion associated with a first side of a joint;
a second set of sensors attachable to a second body portion associated with a second side of the joint, wherein the first set of sensors sense at least one selected from the group of linear acceleration, rotational velocity, and orientation of the first body portion and the second set of sensors sense at least one selected from the group of linear acceleration, rotational velocity, and orientation of the second body portion; and
at least one processor configured to:
distinguish portions of the first and second data sets corresponding to static events of the first and second body portions and events when the first and/or second sets of sensors have been removed; and
truncate the first and second data sets to remove the portions of the first and second data sets corresponding to events when the first and/or second sets of sensors have been removed.

24. The movement monitoring system of claim 23, wherein the at least one processor is configured to distinguish between static events of the first and second body portions and events when the first and/or second sets of sensors have been removed using an acceleration and/or movement threshold.

25. The movement monitoring system of claim 23, wherein the at least one processor is configured to identify an orientation of the first data set and an orientation of the second data set, and orient the first and second data sets to a common coordinate frame.

26. The movement monitoring system of claim 23, wherein the at least one processor is configured to determine movement of the first body portion relative to the second body portion using the truncated first and second data sets.

27. The movement monitoring system of claim 26, wherein the at least one processor is further configured to:
determine a movement metric for the joint with the determined relative movement of the first and second body portions;
determine a difference between the determined movement metric and a standard movement metric; and
determine if intervention is needed for the subject based at least in part on the difference between the determined movement metric and the standard movement metric.

28. The movement monitoring system of claim 27, wherein the at least one processor is further configured to output an indication of whether or not intervention for the subject is needed.

29. The movement monitoring system of claim 27, wherein the standard movement metric is a function of time.

30. The movement monitoring system of claim 27, wherein the at least one processor is configured to determine that a first intervention is needed if the difference between the determined movement metric and the standard movement metric exceeds a first threshold and to determine that a second intervention is needed if the difference between the determined movement metric and the standard movement metric exceeds a second threshold.

* * * * *